United States Patent [19]

Doyle et al.

[11] Patent Number: 5,354,661
[45] Date of Patent: Oct. 11, 1994

[54] MONOCLONAL ANTIBODY TO ENTEROHEMORRHAGIC *ESCHERICHIA COLI* 0157:H7 AND 026:H11 AND METHOD FOR DETECTION

[75] Inventors: Michael P. Doyle, Peachtree City; Nisha Padhye, Atlanta, both of Ga.

[73] Assignee: Wisconsin Alumni Research Foundation, Madison, Wis.

[21] Appl. No.: 842,384

[22] PCT Filed: Jul. 26, 1991

[86] PCT No.: PCT/US91/05310

§ 371 Date: May 26, 1992

§ 102(e) Date: May 26, 1992

Related U.S. Application Data

[63] Continuation-in-part of Ser. No. 559,867, Jul. 19, 1990, Pat. No. 5,168,063.

[51] Int. Cl.$^5$ .................. G01N 33/569; G01N 33/535
[52] U.S. Cl. .......................... 435/7.37; 435/34; 435/38; 435/7.92; 435/240.27; 435/849; 530/388.4; 530/350; 530/825
[58] Field of Search ............... 530/825, 388.4, 350; 435/29, 34, 38, 7.37, 7.92, 240.27, 849

[56] References Cited

U.S. PATENT DOCUMENTS

| | | | |
|---|---|---|---|
| 5,100,801 | 3/1992 | Ward et al. | 435/296 |
| 5,168,063 | 12/1992 | Doyle et al. | 435/240.27 |

OTHER PUBLICATIONS

Siragusa, G. R., et al., "Persistence of Listeria-monocytogenes in Yogurt as Determined by Direct Plating and Enrichment Methods," *Int. J. Food Microbiol.* 7, pp. 147–160, 1988, Abstract only.

Doyle, M. P., et al., "Isolation of *Escherichia coli* 0157:H7 from Retail Fresh Meats and Poultry," *Applied and Environmental Microbiology*, vol. 53, No. 10, pp. 2394–2396, Oct. 1987.

Bopp, C. A., et al., 1987, "Unusual Verotoxin–Producing *Escherichia coli* Associated with Hemorrhagic Colitis," *J. Clin. Microbiol.*, vol. 25, pp. 1486–1489.

Hancock, R. E. W. and H. Naikaido, 1987, "Outer Membranes of Gram–Negative Bacteria," *Journal of Bacteriology*, vol. 136, pp. 381–390 (isolating of outer membrane proteins).

Karmali, M. A. et al., 1983, "Sporadic Cases of Hemolytic Uremic Syndrome Associated with Fecal Cytoxin and Cytoxin Producing *Escherichia coli* in Stools," *Lancet*, vol. i, pp. 619–620.

Levine, M. M., 1987, "*Escherichia coli* that Cause Diarrhea: Enterotoxigenic, Enteropathogenic, Enteroinvasive, Enterohemorrhagic, and Enteroadherent," *Journal of Infectious Diseases*, vol. 155, pp. 377–389.

Levine, M. M., et al., 1987, "A DNA Probe to Identify Enterohemorrhagic *Escherichia coli* of 0157:H7 and Other Serotypes that Cause Hemmorhagic Colitis and Hemolytic Uremic Syndrome," *Journal of Infectious Diseases*, vol. 156, pp. 175–182.

Padhye, N. P. and M. P. Doyle, 1990, "Production and Characterization of Monoclonal Antibody to *Escherichia coli* 0157:H7", *Amer. Soc. for Microb. (Annual Mtg.)* (Abstract), P-14, p. 280.

Padye, V. V., et al., 1990 "Production and Characterization of Monoclonal Antibodies to Verotoxins 1 and 2 from *Escherichia coli* of Serotype 0157:H7," *Biological Abstracts*, vol. 89, No. 5, the abstract No. 48707.

Padhye, V. V. et al., 1989, "Production and Characterization of Monoclonal Antibodies to Verotoxins 1 and 2 from *Escherichia coli* of Serotype 0157:H7," *J. Med. Microb.*, vol. 30, pp. 219–226.

(List continued on next page.)

*Primary Examiner*—Toni R. Scheiner
*Attorney, Agent, or Firm*—Ross & Stevens

[57] ABSTRACT

A monoclonal antibody specific for enterohemorrhagic *Escherichia coli* 0157:H7 and 026:H11 is produced by immunizing BALB/c mice with a strain of *E. coli* 0157:H7. The antibody reacts strongly by an enzyme-linked immunosorbent assay with an approximately 5,000–6,000 dalton molecular weight outer membrane protein of strains of enterohemorrhagic *Escherichia coli* 0157:H7 and 026:H11. A rapid and sensitive assay for detecting these organisms is also disclosed.

20 Claims, 3 Drawing Sheets

OTHER PUBLICATIONS

Perera, L. P., et al., 1988, "Isolation and Characterization of Monoclonal Antibodies to Shiga–Like Toxin II of Enterohemorrhagic *Escherichia coli* and Use of the Monoclonal Antibodies in a Colony Enzyme–Linked Immunosorbent Assay," *Journal of Clinical Microbiology*, vol. 26, No. 10, pp. 2127–2131, see the Abstract.

Perry, M. B. et al., 1988, "Identification of *Escherichia coli* Serotype 0157 Strains by Using a Monoclonal Antibody," *J. Clin. Microbiol.*, vol. 26, pp. 1973–1978.

Pollard, D. R. et al., 1990, "Rapid and Specific Detection of Verotoxin Genes in *Escherichia coli* by the Polymerase Chain Reaction", *J. Clin. Microb.*, vol. 28, pp. 540–545.

Riley, Lee W. et al, 1983, "Hemorrhagic Colitis Associated With A Rare Escherichia Coli Serotype," *The New England Journal of Medicine*, vol. 308, No. 12, pp. 681–685.

Ryan, Caroline A. et al, 1986, "*Escherichia coli* 0157:H7 Diarrhea in a Nursing Home: Clinical, Epidemiological, and Pathological Findings," *Journal of Infectious Diseases*, vol. 154, No. 4, pp. 631–638.

Samadpour, M. et al., 1990, "Evaluation of DNA probes for detection of Shiga–Like–Toxin Producing *Escherichia coli* in Food and Calf Fecal Samples," *Appl. and Envir. Microb.*, vol. 56, pp. 1212–1215.

Smith et al., 1985, "Measurement of Protein Using Bicinchoninic Acid," *Analytical Biochemistry*, vol. 150, pp. 76–85 (determination of protein concentration).

Todd, E. C. D. et al, 1988, "Rapid Hydrophobic Membrane Filter–Enzyme Labeled Antibody Procedure for Identification and Enumeration of *Escherichia coli* 0157:H7 in Foods" *Applied and Environmental Microbiology*, vol. 54, pp. 2536–2540.

Tzipori, S., et al., 1988, "Studies in Gnotobiotic Piglets on Non–0157:H7 *Escherichia coli* Serotypes Isolated from Patients with Hemorrhagic Colitis," *Gastroenterology*, vol. 94, No. 9, pp. 590–597, see the abstract.

MONOCLONAL ANTIBODY TO ENTEROHEMORRHAGIC *ESCHERICHIA COLI* 0157:H7 AND 026:H11 AND METHOD FOR DETECTION

REFERENCE TO RELATED APPLICATION

This is a continuation of PCT Application No. U.S. 91/05310, filed Jul. 26, 1991, which is a continuation-in-part of U.S. application No. 07/559,867, filed Jul. 27, 1990 now U.S. Pat. No. 5,168,063.

FIELD OF THE INVENTION

The present invention relates generally to hybridoma cell lines developed to produce monoclonal antibodies and, more specifically, to a cell line producing monoclonal antibodies to enterohemorrhagic *Escherichia coli* 0157:H7 (*E. coli* 0157:H7) and *Escherichia coli* 026:H11 (*E. coli* 026:H11).

DESCRIPTION OF THE PRIOR ART

*E. coli* 0157:H7 was first recognized as an important human pathogen in the United States in 1982, when the organism was diagnosed as the cause of two geographically separate outbreaks of hemorrhagic colitis, both associated with eating undercooked beef from a particular fast-food chain, (Riley, Lee W. et al, 1983, "Hemorrhagic Colitis Associated With A Rare *Escherichia Coli* Serotype," *The New England Journal of Medicine*, Vol. 308, No. 12, pgs. 681-685). These outbreaks of unusual gastrointestinal illness were characterized by the sudden onset of severe abdominal cramps and grossly bloody diarrhea with no fever or low grade fever. Such illnesses have been associated with *E. coli* 0157:H7 and also *E. coli* 026:H11 (Levine, M. M. 1987, "*Escherichia coli* that Cause Diarrhea: Enterotoxigenic, and Enteropathogenic, Enteroinvasive, Enterohemorrhagic, and Enteroadherent," *Journal of Infectious Diseases*, vol. 155, pgs 377-389; Levine, M. M., et al, 1987, "A DNA Probe to Identify Enterohemorrhagic *Escherichia coli* of 0157:H7 and Other Serotypes that Cause Hemmorhagic Colitis and Hemolytic Uremic Syndrome," *Journal of Infectious Diseases*, vol. 156, pgs. 175-182). These bacteria are termed enterohemorrhagic *E. coli*.

The *E. coli* organism produces toxins, known as verotoxins, that cause significant intestinal bleeding in several mammals, including humans. The spectrum of illnesses associated with *E. coli* 0157:H7 infections ranges from asymptomatic infections to non-bloody diarrhea, hemorrhagic colitis, hemolytic uremic syndrome and death (Ryan, Caroline A et al, 1986, "*Escherichia coli* 0157:H7 Diarrhea in a Nursing Home: Clinical, Epidemiological, and Pathological Findings," *Journal of Infectious Diseases*, Vol. 154, No. 4, pgs. 631-638). Hemolytic uremic syndrome is defined as the sudden onset of hemolytic anemia, thrombocytopenia and acute renal failure after the appearance of symptoms in the upper respiratory tract, stomach or intestines. Hemolytic uremic syndrome is generally the end result of a number of different and inciting events and pathogenic mechanisms.

The organism has been isolated from meat and poultry and unpasteurized milk. A variety of reports suggest that foods, particularly foods of animal origin, may be an important source of *E. coli* 0157:H7 infections (Doyle, Michael P. and Jean L. Schoeni, 1987, "Isolation of "Escherichia Coli 0157:H7 from Retail Fresh Meats and Poultry," *Applied and Environmental Microbiology*, vol. 53, No. 10, pgs. 2394-2396).

Because most of the outbreaks of hemorrhagic colitis have been food related, there is a need for a rapid, sensitive and specific assay for detecting *E. coli* 0157:H7 and *E. coli* 026:H11. Presently, the available methods for detecting the organism in foods are time consuming or are not highly specific. For example, the Food Research Institute, Madison, Wis., is currently being used by many agencies for the detection of the *E. coli* 0157:H7 organism. The process utilized by the Food Research Institute, however, involves a complicated, multi-day procedure described in Doyle and Schoeni (supra). Doyle and Schoeni have tested a variety of meats and found the organism in about 1% or 2% of the meats tested. The organism can also be isolated from feces, raw milk, etc. Eggs from experimentally infected chickens are also contaminated on the surface.

In order to assay the organism, the first step is to enrich the organism in the food sample. Because the food sample may have minor amounts of the organism, the sample is placed in an enrichment media to put it in a condition which should repress other forms of bacteria and increase the numbers of the desired organism. The enrichment medium has selective agents which are selective for gram-negative bacteria, including *E. coli* 0157:H7. The medium is then incubated overnight at 37° C.

The incubated sample is then run through a hydrophobic grid membrane filter paper (HGMF). The filter paper is subdivided into about 1,400–1,600 little squares. Wax is used to mark the filter off. The wax keeps the colonies isolated. The filter is then removed and placed on a piece of nitrocellulose paper. The nitrocellulose paper will be placed over some of the medium with agar that contains the same selective agents as in the enrichment medium. This plate is then incubated at 37° C. overnight. This allows the colonies to develop on the filter paper. As they grow, they elaborate verotoxins. The toxins are trapped in the nitrocellulose paper. The filter paper is then removed and saved. The nitrocellulose paper is then removed and developed by an immunoblot procedure which employs antibodies produced-in rabbits to the toxins. After the blots are developed, spots are observed on the paper where toxin is present. The spots on the HGMF are matched with the bacterial colonies on the HGMF, and the matching colonies are then confirmed as the target *E. coli* 0157:H7 by biochemical or other tests.

In summary, the organism is grown in the food sample in a selective enrichment medium. The organism is then isolated in a series of procedures. The separated isolates grow to produce toxins which diffuse into and are entrapped in an underlying filter paper. The toxins are then detected using antibody to the toxins as a reagent. Bacterial colonies on the overlying filter paper with grids are aligned with the filter paper showing spots with toxin. Colonies that produced toxin are identified by standard taxonomic procedures.

Although the procedure can effectively isolate *E. coli* 0157:H7 from food samples inoculated with low levels of the organism, the method is not amenable to routine testing because of complexity and extensive need for personnel time.

Other tests, such as one developed by Health and Welfare Canada, are being developed. The Canadian test uses a monoclonal antibody to *E coli* 0157, but it is not a specific test because it cross-reacts with other enterics, such as salmonella Group N and unimportant *E. coli* 0157 strains that are not H7. (Todd, E. C. D. et al, 1988, "Rapid Hydrophobic Membrane Filter-Enzyme Labeled Antibody Procedure for Identification and Enumeration of *Escherichia coli* 0157:H7 in Foods" *Applied and Environmental Microbiology*, vol. 54, pgs. 2536–2540.)

Gene-probe based assays have been developed which are based on binding DNA that encodes for verotoxins (Levine, M. M., et al., supra. 1987). Hence, all verotoxin-producing *E. coli* are detected by this procedure rather than solely enterohemorrhagic *E. coli* 0157:H7 and *E. coli* 026:H11.

SUMMARY OF THE INVENTION

It is an object of the present invention to produce a monoclonal antibody that is highly specific for enterohemorrhagic *E coli* 0157:H7 and *E coli* 026:H11.

It is further an object of the present invention to develop a test for using a monoclonal antibody to assay *E coli* 0157:H7 and *E. coli* 026:H11 in which the procedure is shortened to a usable period of time, e.g., under one day.

It is further an object of the present invention to develop an immunoassay for the rapid detection of *E. coli* 0157:H7 and *E coil* 026:H11 in food and fecal specimens.

It is another object of the present invention to develop a procedure to isolate *E. coli* 0157:H7 and *E. coli* 026:H11 from foods or other samples and to determine the prevalence of the organisms in the samples.

It is another object of this present invention to use a specified outer membrane protein of enterohemorrhagic *E. coli* 0157:H7 and *E. coli* 026:H11 as a marker to identify strains of enterohemorrhagic *E. coli*. Assays, including ELISA, based on monoclonal antibody specific to this marker, will be used to detect and differentiate enterohemorrhagic *E. coli* isolated from foods, environmental and clinical specimens.

It is further an object of the present invention to provide for the synthesis of a bioreagent for antibody assays, which will be useful in a test kit for, for example, assaying the presence of enterohemorrhagic *E. coli* 0157:H7 and *E. coli* 026:H11.

The present invention is summarized in that a monoclonal antibody specific to enterohemorrhagic *E coli* 0157:H7 and *E. coli* 026:H11 is produced by a hybridoma formed by the fusion of cells from a mouse myeloma line and spleen cells from a mouse previously immunized with a "rough" strain of *E. coli* 0157:H7. This rough strain was modified so that it lacks smooth lipopolysaccharides, which includes expression of 0157 antigen, on its cell surface. The monoclonal antibody is characterized in that it reacts with a protein having a molecular weight of approximately 5,000–6,000 daltons. The protein is a part of the outer membrane proteins of enterohemorrhagic *E coli* 0157:H7 and *E. coli* 026:H11. This protein has apparent specificity for enterohemorrhagic *E. coli* 157:H7 and *E. coli* 026:H11. The monoclonal antibody is further characterized in that it is a member of the subclass immunoglobulin $G_{2a}$ and it has a kappa light chain.

The present invention is further directed to a method of assaying for the presence of *E. coli* 0157:H7 in a test sample, comprising the steps of binding polyclonal antibody to *E. coli* 0157 to adsorptor substrate units to produce antibody to *E. coli* 0157-charged substrate units, exposing a known quantity of the test material to the antibody *E. coli* 0157-charged substrate unit so as to cause the antibody to bind to any *E. coli* 0157:H7 organism present in the test material to produce a reacted unknown sample, exposing a selected quantity of a standard preparation of *E. coli* 0157:H7 organism having a known amount of *E. coli* 0157:H7 to the antibody to *E. coli* 0157-charged substrate unit to create a reacted control sample, exposing the reacted unknown and control samples to a monoclonal antibody (4E8C12) to *E. coli* 0157:H7 to react with the bound *E coli* 0157:H7, removing monoclonal antibody not reacted with the bound *E. coli* 0157:H7 on the antibody to *E. coli* 0157-charged substrate units and comparatively and quantitatively assaying for the presence of reacted monoclonal antibody on the first and second antibody to *E. coli* 0157-charged substrate units.

The present invention is further directed to a process for producing monoclonal antibodies against enterohemorrhagic *E. coli* 0157:H7 and *E. coli* 026:H11 comprising propagating a hybridoma formed by fusing a cell capable of producing antibodies against enterohemorrhagic *E. coli* 0157:H7 and *E. coli* 026:H11 with a myeloma cell and harvesting the antibodies produced by the hybridoma.

The present invention is also directed to a diagnostic kit for assaying the presence of enterohemorrhagic *E. coli* 0157:H7 and/or *E. coli* 026:H11 comprising the monoclonal antibody specific to enterohemorrhagic *E coli* 0157:H7 and *E. coli* 026:H11 and directions for its use.

The present invention is also directed to a bioreagent for antibody assays comprising a substantially pure protein having a molecular weight of about 5,000–6,000 daltons. The protein is found in the outer membrane of *E. coli* 0157:H7 or *E. coli* 026:H11, and is capable of reacting specifically with monoclonal antibodies to *E coli* 0157:H7 and *E. coli* 026:H11.

The present invention is also directed to a substantially pure protein found in the outer membrane of *E coli* 0157:H7 or *E. coli* 026:H11 having a molecular weight of about 5,000–6,000 daltons and being capable of reacting specifically with monoclonal antibodies to *E. coli* 0157:H7 and *E. coli* 026:H11.

Because of its high specificity, the monoclonal antibody may be a useful reagent for the rapid detection of enterohemorrhagic *E. coli* 0157:H7 and/or *E. coli* 026:H11 in foods and in clinical specimens. Further, the testing procedure should be reduced to one day or less. The testing procedure would include, first, growing the organism on a selected growth medium and, then, testing for its presence by, for example, enzyme-linked immunosorbent assays (hereinafter ELISAs) and other immunoassays.

The present invention is also directed to a specific and sensitive procedure for detecting *E. coli* 0157:H7 in a substrate such as food. The procedure involves the enrichment of the substrate in a selective enrichment medium containing acriflavin (also spelled acriflavine) to form an enriched culture. The enriched culture is applied to an assay, such as an ELISA assay. In addition to being highly specific and sensitive, the procedure is rapid, easy to perform and is amenable to use by laboratories performing routine microbiological testing. The presumptive positive identification of *E. coli* 0157:H7 in a substrate can be done in less than 20 hours. The organism can be isolated and confirmed as *E. coli* 0157:H7 within 2 days after presumptive positive detection.

Other objects and advantages of the invention will be apparent from the following detailed description and figures setting forth the preferred embodiment of the invention.

DETAILED DESCRIPTION OF THE PREFERRED EMBODIMENT

Enterohemorrhagic *E. coli* 0157:H7 and *E. coli* 026:H11 have been identified as important human pathogens. They produce one or more toxins (verotoxins) that cause significant intestinal bleeding in several mammals, including humans. The organism is sometimes fatal. It is found in raw milk, raw supermarket meats, etc. and presumably introduced by fecal contamination. Some of the characteristics of *E. coli* 0157:H7, as described in Ryan et al (supra, 1988), are as follows. *E. coli* 0157:H7 does not produce heat stable or heat labile enterotoxins. It is not invasive and does not adhere to HeLa cells. It does produce high levels of a Vero cytotoxin that appears to be similar to Shiga toxin. *E. coli* has been shown to produce one or more different Vero cell cytotoxins, as described in Padhye, Vikas V. et al., 1989, "Production and Characterization of Monoclonal Antibodies to Verotoxins 1 and 2 from *Escherichia coli* of Serotype 0157:H7," *Journal of Medical Microbiology*, Vol. 30, pgs. 219–226.

*E. coli* 026:H11 is similar to *E. coli* 157:H7 in that both are enterohemorrhagic *E. coli* that produce verotoxin and cause hemolytic uremic syndrome and hemorrhagic colitis (Bopp, C. A., et al , 1987, "Unusual Verotoxin-Producing *Escherichia coli* Associated with Hemorrhagic Colitis," *J. Clin Microbiol.*, Vol. 25, pgs. 1486–1489; Karmali, M. A. et al., 1983, "Sporadic Cases of Hemolytic Uremic Syndrome Associated with Fecal Cytoxin and Cytoxin Producing *Escherichia coli* in Stools," *Lancet*, Vol. i, pgs. 619–620; Levine, M. M., supra., 1987).

In general overview, a monoclonal antibody, designated 4E8C12, specific for *E. coli* 0157:H7 and *E. coli* 026:H11 was produced by immunizing BALB/c mice with a "rough" strain of *E. coli* 0157:H7 deficient of the 0157 antigen. Spleen cells from the mice so immunized were fused with a mouse myeloma cell, with the fusion being effected with treatment in polyethylene glycol in accord with known methods. The resulting hybridomas were cultured and then selected for antibody activity. The cells producing antibodies specific to *E. coli* 0157:H7 and *E. coli* 026:H11 were detected by means of an ELISA, in the manner well known to the art. The antibody was purified from ascites fluid in conventional ways. The cloned cell line so created and selected was perpetuated by conventional cell culturing techniques.

The hybridoma produced in this manner was deposited at the American Type Culture Collection 12301 Parklawn Drive, Rockville Md. 20852, USA on May 10, 1990, and has been assigned the designation HB 10452. This particular hybridoma and the antibodies produced thereby are the hybridoma and monoclonal antibodies referred to below, unless otherwise stated. A detailed description of the making of the hybridoma is included below. Future reference to the hybridoma is as follows: ATCC HB 10452.

This deposit is made under the provisions of the Budapest Treaty on the International Recognition of the Deposit of Microorganisms for the Purposes of Patent Procedure and the Regulations thereunder (Budpest Treaty). This assures maintenance of a viable culture for 30 years from the date of deposit. The organism will be made available by ATCC under the terms of the Budapest Treaty, and subject to an agreement between applicants and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto including 37 CFR §1.14 with particular reference to 886 OG 638). The assignee of the present application agrees that if the culture on deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

In contrast with previously reported references, which disclose monoclonal antibodies that react with *E. coli* 0157:H7 but also bind to the somatic 0157 antigen and hence react with all *E. coli* belonging to the serogroup 0157 (Perry, M. B. et al., 1988, "Identification of *Escherichia coli* Serotype 0157 Strains by Using a Monoclonal Antibody," *J. Clin. Microbiol.*, Vol 27, pgs. 1973–1978), the monoclonal antibody of the present invention does not react with the 0157 antigen and is, with the exception of one other serotype of *E. coli*, very specific for *E. coli* 0157:H7. The other serotype is *E. coli* 026:H11. As used herein, the phrase "specific for *E. coli* 0157:H7 and *E. coli* 026:H11" is intended to mean that the monoclonal antibody of the present invention does not react with the strains of *E. coli* listed on Table 2 in Example 1, other than the listed strains of *E. coli* 0157;H7 and *E. coli* 026: H11.

The antibodies were tested for specificity by ELISAs and by immunoblotting of a variety of enterics. By these means, it was determined that the monoclonal antibody forms a strong reaction by direct ELISA with each of 36 strains of *E. coli* 0157:H7 and 5 strains of *E. coli* 026:H11. However, there was no cross-reactivity with strains of other enterics such as, for example, Salmonella, *Yersinia entrocolitica*, Shigella, Proteus, Klebsiella, *Campylobacter jejuni*, Serratia, *Aeromonas, hydrophila*, Citrobacter, Enterobacter, Hafnia, *Escherichia hermanii*, and all other strains of *E. coli* other than the serotypes 0157:H7 and 026:H11 (including strains of serotype 0157 but not H7).

Studies on the monoclonal antibody to *E. coli* 0157:H7 and 026:H11 show that the monoclonal antibody (Mab) has the following characteristics: (1) it is a member of the subclass IgG$_{2a}$; (2) it has a kappa light chain; and (3) it reacts specifically with an outer membrane protein of enterohemorrhagic *E. coli* 0157:H7 and *E. coli* 026:H11 having a molecular weight of approximately 5,000–6,000 daltons, as determined by SDS-polyacrylamide gel electrophoresis of outer membrane proteins of *E. coli* of different serotypes followed by Western blot analysis.

Originally, the outer membrane protein of enterohemorrhagic *E. coli* 0157:H7 and *E. coli* 026:H11 was believed to have a molecular weight of about 13,000 daltons. The molecular weight determination was made using a 15% sodium dodecyl sulphate - polyacrylamide gel electrophoresis (SDS-PAGE) system to resolve the protein. The protein appeared as a doublet, i.e., two closely related bands. The doublet was believed to represent one protein in the outer membrane of the microorganisms having a molecular weight of approximately 13,000 daltons.

Evidence now indicates that the aforementioned system was not efficient to resolve low molecular weight proteins (Padhye, N. V. and M. P. Doyle, Jan. 1991, *J. Clin. Microb.*, 29(1):99–103). The outer membrane protein most likely has an apparent molecular weight of approximately 5,000–6,000 daltons. The cellular component of *E. coli* 0157:H7 and 026:H11 that reacted with Mab 4E8C12 was determined by tricine-SDS-PAGE (Schagger, H. and G. Jagow, 1987, *Anal. BioChem.* 166: 368–379) followed by Western immunoblot analysis.

Figure 1A:
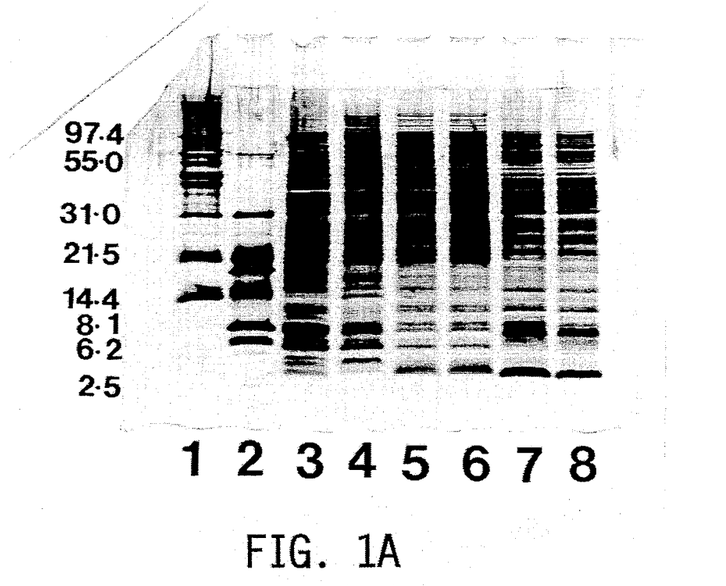
FIG. 1A is a photograph illustrating the tricine-SDS-PAGE profile of outer membrane proteins (OMP) of *E coli* 0157:H7 strain 932 (lane 3), *E. coli* HA1 (lane 4), *E. coli* 026:H11 strain 94–381 (lane 5), *E. coli* 026:H11 strain 89–326, *E. coli* 0157:H16 (lane 7), and *E. coli* 0157:H45 (lane 8). A 5 μg sample of OMP was applied per lane. Low-molecular weight standards (indicated on the left, in thousands) are shown in lanes 1 and 2. The gel was silver stained.
Figure 1B:
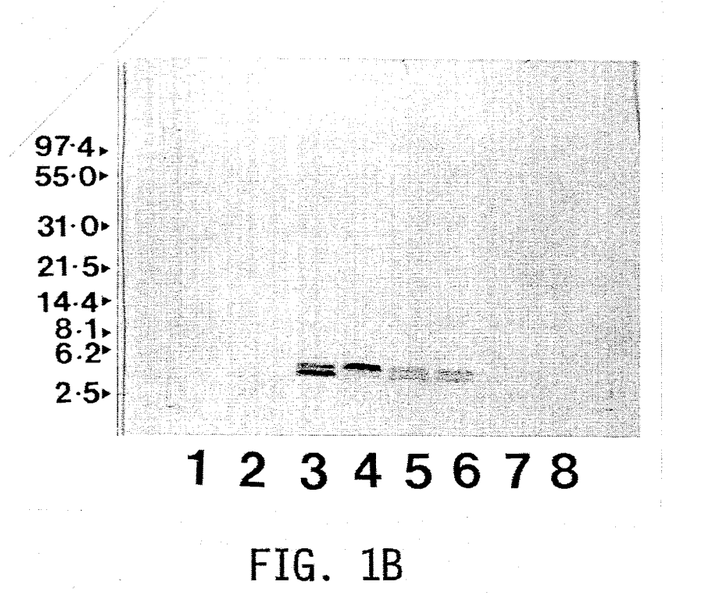
FIG. 1B is a photograph illustrating a Western blot of SDS-PAGE-separated OMPs treated with MAb 4E8C12. Lane numbers correspond with the OMP preparations indicated in FIG. 1A.

The outer membrane proteins (OMP) from *E. coli* 0157:H7 strain 932, *E. coli* HA1, *E coli* 0157:H16, *E. coli* 0157:H45 and *E. coli* 026:H11 were separated by a special tricine-SDS-PAGE procedure because of the necessity to separate low-molecular weight proteins with high resolution. Reference is made to FIG. 1A. The separated proteins from a second gel were transferred to a polyvinyl difluoride membrane, and the location of antigen recognized by Mab 4E8C12 was determined by Western blot analysis. The Mab reacted with two 5,000–6,000 molecular weight OMP's of *E. coli* 0157:H7 strain 932, *E. coli* HA1 and *E. coli* 026:H11 as illustrated in FIG. 1B. No cross-reaction was observed with either *E. coli* 0157:H16 or *E. coli* 0145:H45.

The determination of molecular weight was confirmed by additional tests on the amino acid compositions of the bands. The amino acid compositions of both the bands as well as the purified protein (purified using high performance liquid chromatography or HPLC) were nearly identical with only some slight variation as illustrated below in Table 1.

TABLE 1

| Amino Acid Composition of Targeted Outer Membrane Protein | | | |
|---|---|---|---|
| | No. of residues based on 50 amino acids | | |
| Amino Acid | Lower Band | Upper Band | Protein after HPLC |
| Aspartic Acid | 4 | 5 | 4 |
| Threonine | 2 | 3 | 2 |
| Serine | 4 | 6 | 6 |
| Proline | 2 | 2 | 1 |
| Glycine | 10 | 10 | 9 |
| Alanine | 4 | 5 | 4 |
| Methionine | 1 | 1 | 1 |
| Isoleucine | 2 | 2 | 2 |
| Leucine | 4 | 5 | 4 |
| Tyrosine | 1 | 1 | 1 |
| Phenylalanine | 2 | 2 | 2 |
| Histidine | 1 | 1 | 1 |
| Lysine | 2 | 2 | 2 |
| Arginine | 2 | 2 | 2 |
| Glutamic Acid | 7 | 6 | 6 |

A certain percentage of discrepancy is expected because upon hydrolysis some amino acids are oxidized to variable extents yielding different numbers of residues each time. However, the number of stable amino acids such as tyrosine, phenylalanine, histidine, lysine and arginine is constant in all the three proteins.

Thus, it is believed that the targeted outer membrane protein is at least one protein having an apparent molecular weight of approximately 5,000–6,000. Aside from the amino acid composition of the outer membrane protein(s), other evidence which supports that the outer membrane protein is one protein having a molecular weight of approximately 5,000–6,000 includes a common isoelectric point; common epitopes on both the protein bands recognized by the monoclonal antibody 4E8C12, and a single peak disclosed after HPLC purification.

ELISAs are a conventional method for assaying for the presence of an antigen in a sample of test material. The sandwich ELISA of the invention is adapted to assay for the presence of enterohemorrhagic *E. coli* 0157:H7 in a sample of test material and includes the following steps. First, a known antibody to *E. coli* 0157 is bound to a suitable adsorptor substrate. Preferably, a plastic culture plate is used, such as a 96-well polystyrene culture plate (Costar, Cambridge, Mass.—Model No. 3596). A Solution of antibody to *E. coli* 0157 is placed in each of the wells and allowed to remain under conditions such that the antibody to *E. coli* 0157 is adsorbed to the surface of the wells. Unabsorbed antibody solution is then washed away, leaving the antibody to *E. coli* 0157 bound to the adsorptive walls of the wells, which shall be referred to as "adsorbtor substrate units." With antibody to *E. coli* 0157 adsorbed to them, they shall be referred to as "antibody to *E. coli* 0157-charged substrate units." The antibody to *E. coli* 0157-charged substrate units is then treated with an appropriate blocking reagent, such as nonfat dried milk, to block non-specific binding sites. After appropriate incubation, this reagent is removed.

Next, a known quantity of the test material is exposed to the antibody to *E. coli* 0157-charged substrate units for an appropriate period of time, and then is removed by washing. Any *E. coli* 0157:H7 in the test material will bind to the antibody to *E. coli*-charged substrate units.

Similarly, a standard preparation of *E. coli* 0157:H7 is exposed to another set of antibody to *E. coli* 0157-charged substrate units to serve as a control.

The monoclonal antibody referred to above is added to the antibody to *E. coli* 0157-charged substrate units to bind with any bound *E. coli* 0157:H7. After appropriate incubation, unbound the monoclonal antibody is removed by washing.

The antibody to *E. coli* 0157-charged substrate units reacted with test samples or *E. coli* 0157:H7 are then assayed for the presence of monoclonal antibody.

Preferably this is done by exposing antibody to *E. coli* 0157-charged substrate units reacted with the test samples or *E. coli* 0157:H7 and the monoclonal antibody thereon to a marker-coupled anti-mouse antibody to allow the marker-coupled antibody to bind to any monoclonal antibody present. The unbound marker-coupled antibody is then removed, and the amount of marker remaining on the antibody to *E. coli* 0157-charged substrate units is measured. The marker may be an enzyme measured by its effect on a selected reagent, a fluorescent material, a radioactive material, or any other of the markers familiar to one skilled in the art. It will be apparent that the monoclonal antibody itself may be combined directly with a marker, whereupon the step of reacting a marker-coupled anti-mouse antibody may be omitted.

The monoclonal antibody may also be used in other conventional ELISAs. For example, a sample of test material may be bound to an adsorbtor substrate and then exposed to the monoclonal antibody disclosed above. The antibody binds to any *E. coli* 0157:H7 or *E. coli* 026:H11 present in the test material. Unbound portions of the monoclonal antibody are then removed. Next, an assay comparable to those discussed above is conducted for the presence of bound monoclonal antibody.

The monoclonal antibody of the present invention may also be used in any of the generally known methods of using such antibodies in immunohistological techniques for examining a substantially cohesive, nonfluid test material, such as a cell or tissue sample. Preferably, the sample is a food product or a fecal sample. The test material is incubated with the monoclonal antibody to bind the antibody to *E. coli* 0157:H7 or *E. coli* 026:H11 present in the test material. The test material is then washed to remove the unbound portion of the monoclonal antibody. The antibody may then be reacted in such a way as to make its presence visually apparent. Typically, the test material bearing monoclonal antibody bound to *E. coli* 0157:H7 or *E. coli* 026:H11 contained therein is incubated with a marker-labeled anti-mouse antibody comparable to those discussed above. The marker-labeled antibody binds to the monoclonal antibody. A marker is selected such that it may be made visually apparent. Fluorescent and enzyme markers typically are used. The test material is then microscopically observed under conditions adapted to render the marker visually perceivable. The monoclonal antibody to *E. coli* 0157:H7 and *E. coli* 026:H11 is specifically useful as a reagent for the rapid detection of *E. coli* 0157:H7 and/or *E. coli* 026:H11 in food and clinical specimens.

The method for assaying the presence of an antigen in a test material can be enhanced by using a selective enrichment medium to enrich the test material prior to assay. The enrichment medium is a modified trypticase soy broth (mTSB), formulated by Doyle and Schoeni (supra, 1987), which has been further modified to include acriflavin-Hcl and casamino acids. We found the both acriflavin-Hcl and casamino acids substantially enhances antigen expression by *E. coli* 0157:H7. In addition, casamino acids enhance the growth of *E. coli* 0157:H7, and acriflavin-Hcl inhibits the growth of gram-positive bacteria. Although the exact mechanism by which acriflavin-HCl enhances the antigen expression by *E. coli* 0157:H7 is not known, it is believed that it may be a consequence of the suppression of the formation of the cell wall lipopolysaccharide so that the antigen recognized by the monoclonal antibody is better expressed.

Although a variety of assay techniques as described above may be used to accommodate the enrichment medium, a preferred assay technique is the sandwich ELISA procedure known to the art. For the purposes of this patent application, the herein described assay technique will be designated the "enrichment-sandwich ELISA procedure." The procedure involves enrichment of a test sample or substrate such as food in a selective enrichment medium for approximately 16–18 hours at 37° C. with agitation (150 rpm). The enrichment culture is applied to a sandwich-ELISA that has a polyclonal antibody specific for the *E. coli* 0157:H7 antigen as the capture antibody and a monoclonal antibody specific for enterohemorrhagic *E. coli* of serotypes 0157:H7 and 026:H11 as the detection antibody. The ELISA can be completed within 3 hours.

The enrichment-sandwich ELISA procedure for detection of *E. coli* 0157:H7 described herein is rapid, sensitive and easy to perform. The procedure can detect as few as 0.2 *E. coli* 0157:H7/g of ground beef. *E. coli* 0157:H7 can be detected in less than 20 hours (h), including enrichment. Hence, this procedure can be very useful for routine screening of food samples.

The present invention also includes kits, e.g., diagnostic assay kits, for utilizing the monoclonal antibody to *E. coli* 0157:H7 and *E. coli* 026:H11 and carrying out the method disclosed above. In one embodiment, the diagnostic kit would conventionally include the monoclonal antibody to the *E. coli* 0157:H7 and *E. coli* 026:H11 in one or more containers, a conjugate of a specific binding partner for the monoclonal antibody, a label capable of producing a detectable signal, and directions for its use. The kit may be conjugated to a label, as is well known to the art. Various labels include enzymes, radioisotopes, particulate labels, chromogens, fluorescers, chemiluminescers, coenzymes, free radicals, and bacteriophages. Additionally the monoclonal antibody may be bound to a support.

A specific diagnostic kit could be in a dipstick format. This could involve adsorbing polyclonal *E. coli* 0157 immunoglobulin to a hydrophobic polyvinylidene difluoride (PVDF)-based membrane. The PVDF membrane is then treated with 5% bovine serum albumin to block nonspecific binding sites. The PVDF membrane is dipped for 30 minutes in an enrichment culture of food that may contain *E. coli* 0157:H7. After washing, the PVDF membrane is treated with monoclonal antibody 4E8C12. This antibody will bind to any *E. coli* 0157:H7 cells bound to the PVDF membrane. The bound monoclonal antibody 4E8C12 is detected with alkaline phosphatase-conjugated goat anti-mouse immunoglobulin that reacts with. Nitro blue tetrazolium/5-bromo-4- chloro-3-indolylphosphate substrate to produce purple spots as positive reaction.

The approximately 5,000–6,000 dalton molecular weight protein found in the outer membrane of *E. coli* 0157:H7 and *E. coli* 026:H11 can also be isolated as a bioreagent and used to prepare monoclonal antibodies for detection of *E. coli* 0157:H7 and *E. coli* 026:H11 in a sample. The monoclonal antibodies can be provided in test kits which are used to diagnose cases of suspected *E. coli* 0157:H7 and *E. coli* 026:H11 contamination.

The examples below provide specific examples of the invention disclosed herein.

EXAMPLE I

Preparation of the Cloned Cell Line

Bacterial Strains

Bacterial cultures used to identify specificity of monoclonal antibody: The following strains of bacteria were studied in these examples: *E. coli* 0157:H7 strain 932; *E. coli* HA1 (a rough strain derived from *E. coli* 0157:H7 932), thirty-four other strains of *E. coli* 0157:H7, as listed in the following Table 2, five strains of *E. coli* 026:H11, and thirty-seven strains of *E. coli* other than 0157:H7 or 026:H11, as listed in the following Table 2:

TABLE 2

| *E. coli* Serotype 0157:H7 |
| --- |
| Strain No. |
| 932 |
| 1083-83 |
| CL-8 |
| 1215-83 |
| CL-40 |
| 936-86 |
| 204-P |
| W2-2 |
| EC-13 |
| 100B |
| RPS 386-1 |
| EC-12 |
| SL-19808 |
| 1091-83 |
| A8187 M3 |
| EC-14 |
| 1093-83 |
| SL-20069 |
| NX 0157:H7 |
| 1095-83 |
| 202-P |
| RPS-779 |
| 749-83 |
| HA1 |
| 2790 |
| 28890 |
| 85-1 |
| 85-7 |
| 86-1 |
| 86-7 |
| 87-3 |
| 87-18 |
| 30898-1 MUG |
| 933 |
| 505-B |
| 301-C |
| 929-78 |
| C-600 933W |
| 933-J |
| EC PB40 |
| EC GV50B |
| EC PB-200 |
| EC PB-175 |
| K88 |
| K99 |
| RSF 1030 |
| *E. coli* R1 |
| RP4 |

TABLE 2-continued

| *E. coli* K-12 |
| --- |
| 88-1947 (0157:H16) |
| A2 (0157:H19) |
| 84-1097 (0157:H25) |
| 624-83 (0157:H45) |
| OPHD (0157:H-) |
| 88-573 (02:H7) |
| 88-766 (018:H7) |
| CL-15 (0113:H21) |
| CL-37 (0111:H8) |
| 497-18 (028ac:NM) |
| 0128:B12 |
| 3288-85 (0172:NM) |
| 3056-85 (050:H7) |
| 3030-86 (011:NM) |
| 3377-85 (04:NM) |
| 3153-86 (0125:NM) |
| 75-83 (0145:NM) |
| A96119-C2 (045:H2) |
| 3143-85 (05:NM) |
| 3007-85 (0111:NM) |
| 88-573 (026:H11) |
| 84-381 (026:H11) |
| 105B |
| A-2028 |
| CL-5 (026:H11) |
| 89-386 (026:H11) |
| 3047-86 (026:H11) |

| Bacterial Strains Studied | |
| --- | --- |
| | Strain No. |
| *Shigella dysenteriae* | 4386 |
| | 6611 |
| *Escherichia hermanii* | 89-201 |
| *Proteus mirabilis* | SLH 16606 |
| | MC-3 |
| *Proteus vulgaricus* | 8068 |
| *Serratia marcescens* | 23521 |
| *Salmonella infantis* | 1-2 |
| | 5 |
| | 6S |
| *Salmonella urbana* | 9261 |
| *Salmonella enteritidis* | 11013 |
| *Salmonella typhimurium* | S-7 |
| | S-9 |
| | S-12 |
| | S-15 |
| | E 1297 |
| | S-14 |
| | S-18 |
| | S-19 |
| | E-40 |
| | 9840 |
| *Campylobacter jejuni* | FRI 209 |
| | FRI 205 |
| | FRI 145 |
| | 74C |
| | C122 |
| *Klebsiella pneumoniae* | 272-6 |
| | F182-5(1) |
| | F182-5(2) |
| | F182-6(1) |
| | F184-5(4) |
| | F184-5(5) |
| | F184-6(1) |
| | F188-5(4) |
| | F189-5(2) |
| | F189-5(3) |
| | F189-6(1) |
| | F190-6(3) |
| | F190-7(5) |
| *Klebsiella oxytoca* | 11696 |
| *Citrobacter fruendii* | $Y_6$10RS |
| | $A_2$4R1 |
| | 8027 |
| | JF1 |
| *Citrobacter amalanticus* | 28422 |
| *Citrobacter freundii* | MAT-8 |
| | 6 |
| *Citrobacter diversus* | $MA_1S$-9 |
| | $MA_4S$-9 |
| | 275-6 |

TABLE 2-continued

|                       |          |
|-----------------------|----------|
|                       | LMH 5    |
|                       | 274-8    |
| *Yersinia enterocolitica* | IP-183   |
|                       | IP-162   |
|                       | 2635-NT  |
|                       | 34       |
|                       | 30118    |
|                       | 705      |
|                       | 675      |
|                       | PT-120   |
|                       | Y-7P     |
|                       | PT-63    |
|                       | 736      |
|                       | WA       |
| *Enterobacter cloacae* | 274-6    |
|                       | 272-6    |
| *Hafnia alvei*        | CB-7     |
| *Aeromonas hydrophila* | 7        |
|                       | 12       |
|                       | 17       |
|                       | 23       |

All bacteria were grown in TRYPTICASE® Soy Broth (TSB) (BBL Microbiology Systems, Cockeysville, Md.) at 37° C. for 16–18 hours with agitation (100 rpm).

Toxins

Verotoxins-1 (VT-1) and Verotoxin-2 (VT-2) from *E. Coli* 0157:H7 strain 932 were purified according to the procedures described by Padhye et al. (supra).

Preparation of antigen for inoculation

*E. coli* HA1 cells were grown in TSB at 37° C. for 16 hours with agitation (100 rpm). The cells were harvested by centrifugation (3500 rpm for 10 minutes) and were washed 3 times with 0.01M phosphate buffered saline (pH 7.2). *E. coli* HA1 cells were treated with 2% Formalin and held at 37° C. for 1 week.

Ten BALB/c mice (males, 6–8 weeks old) were immunized by intraperitoneal injection of $2 \times 10^8$ cells of Formalin-treated *E. coli* HA1. Thereafter, every 4 weeks the mice received intraperitoneally the same number of Formalin-treated cells of *E. coli* HA1 until sera obtained by periodic bleeding of mice had titers greater than 1:400. This generally required 3 inoculations. Four days before cell fusion, the mice were given a final intravenous booster injection of $1 \times 10^8$ Formalin-treated cells of *E. coli* HA1. Four to five months after the initial injection, mice were sacrificed and their spleen cells were fused with myeloma cells.

Fusion and cloning

The fusion and cloning process was performed according to the procedure of Galfre, G., 1981, "Preparation of Monoclonal Antibodies: strategies and Procedures, " *Methods in Enzymology*, Vol. 73, pgs. 1–46.) with minor modifications. Briefly, spleen cells from the immunized mice were fused with Sp2/0-Ag-14 myeloma cells using 40% polyethylene glycol (Molecular weight, 1300–1600) (J. T. Baker Chemical Co., Phillipsburg, N.J.) and were grown in selective media containing hypoxanthine, aminopterine, and thymidine (HAT) with 0.3% mouse red blood cells. Supernatant fluids from wells with hybridoma growth were screened for the production of antibodies against *E. coli* 0157:H7 by direct ELISA as described below. Hybridomas of interest were sub-cloned twice by the method of Kohler & Milstein (1975) *Nature*, Vol. 256, pgs. 495–497, by limiting dilution at 0.5 and 0.1 cell/well in a media containing 20% fetal bovine serum (Gibco, Grand Island, N.Y.) and reassayed for antibody production.

Direct ELISA

Antibody production was determined by ELISA performed in a 96-well styrene EIA-RIA plate (Gibco, Grand Island, N.Y.). Each well was coated with 100 microliters (µl) of bacterial cells (*E. coli* 0157:H7 strain 932, *E. coli* 0157:H16, *E. coli* 02:K1:H7, or *E. coli* K-12 (negative control) or $10^7$ cells, optical density of 0.5 at 640 nm) in 50 mM carbonate buffer, pH 9.6, and rotated overnight on an orbital shaker at room temperature. After washing the cells 4 times with 50 mM tris-HCl pH 7.5, plus 150 mM NaCl (TBS), the remaining binding sites were blocked with 5% BSA in TBS. After 1 hour of incubation at 37° C., the blocking buffer was removed and 100 µl of monoclonal antibody (hybridoma supernatant fluid) was added to the wells. The plates were incubated at 37° C. for 1 hour and then the wells were washed 4 times with TBS plus 0.05% Tween-20 (TBS-T). Horseradish peroxidase-conjugated goat anti-mouse IgG (100 µl/well; 1:1400 in TBS) (Kirkegaard & Perry Laboratory, Inc. Gaithersburg, Md.) was added and incubated at 37° C. for 1 hour. After washing the wells 4 times with TBS-T, 100 µl of ABTS-peroxidase substrate (Kirkegaard & Perry Laboratories, Gaithersburg, Md.) was added per well. The enzymatic reaction was stopped with 50 µl of 1% sodium dodecyl sulfate (SDS) in TBS per well after 15 minutes incubation at room temperature. The optical density of reactants in each well was measured by a Dynatech (MR300) microplate reader at 410 nm. Reproducibility of the assay was determined by duplicate testing.

Ascitic fluid

Ten BALB/c mice were primed by intraperitoneal injection of 0.5 ml of 2, 6, 10, 14-tetramethyl pentadecane (Pristane) (Sigma Chemical Co., St. Louis, Mo.). Ten days later mice were injected with $2 \times 10^6$ hybridoma cells. Mouse ascitic fluid was collected from 10 through 20 days after injection. Cell debris and fibrin clots were removed by centrifugation (8000 $\times$g at 10 minutes) and antibody containing fluids were stored at $-20°$ C.

Purification of monoclonal antibodies The monoclonal antibody from the ascitic fluid was purified according to a modification of the manufacturer's instructions using a protein A column (Immunopure plus IgG purification kit, Pierce, Rockford, Ill.). Briefly, ascitic fluid was centrifuged at 10,000$\times$g for 20 minutes and IgG-binding buffer was added (3:1) to the supernatant fluid. This solution (4 ml) was applied to the column and the monoclonal antibody was eluted with IgG-elution buffer. One-ml fractions were collected and protein levels were monitored by measuring (optical density at 280 nm). Fractions with proteins were combined and were dialyzed against 20 mM phosphate buffer, pH 7.0, overnight at 4° C. Finally, the protein concentration was determined according to the procedure described by Smith et al., 1985, "Measurement of Protein Using Bicinchoninic Acid," *Analytical Biochemistry*, vol. 150, pgs. 76–85, using Pierce BCA-protein reagent (Pierce Chemical Co., Rockford, Ill.) and bovine serum albumin as a standard. The activity of purified antibody was determined by direct ELISA and purity was determined by SDS-PAGE.

Immunoglobulin isotyping

Immunoglobulin isotyping was done by ELISA using class specific antisera. Wells of EIA plates were coated with *E. coli* 0157:H7 strain 932 ($10^7$ cells/ml) in 50mM carbonate buffer (pH 9.6). After 4 washes with TBS, nonspecific binding sites were blocked with 5% bovine serum albumin in TBS (W/V). After 1 hour incubation at 37° C., 0.1 ml of the supernatant containing monoclonal antibody 4E8C12 was added to each well and incubation was continued for an additional hour at 37° C. After washing the wells 4 times with TBS-T, rabbit antisera specific individually for mouse IgG, IgG$_{2a}$, IgG$_{2b}$, IgG$_3$, IgM, IgA, kappa or lambda light chains (Mouse-types Isotyping kit, Bio-Rad Laboratories, Richmond, Calif.) were added and held at 37° C. for one hour. The wells were washed 4 times with TBS-T and alkaline phosphatase-labeled goat anti-rabbit IgG (0.1 ml; diluted 1:800 in TBS) was added to each well followed by incubation at 37° C. for 1 hour. After washing the wells 4 times with TBS-T, phosphatase substrate (p-nitrophenylphosphate) (1.0 mg/ml) in 1.0M 2 amino-2 methyl-1-propanol, pH 9.9, was added and an optical density at 41.0 nm was determined after 1 hour incubation at 37° C.

Preparation of outer-membrane proteins

Outer membrane proteins (OMP) were isolated according to the method described by Hancock and Naikaido (Hancock, R. E. W. and H. Naikaido, 1987, "Outer Membranes of Gram-Negative Bacteria," *Journal of Bacteriology*, Vol. 36, pgs. 381–390.), with minor modifications. *E. coli* 0157:H7 strain 932, *E. coli* HA1, *E. coli* 0157:H16, *E. coli* 0157:H45, and *E. coli* CL-5 026:K-60:H11 were grown individually in 2 liters of TSB at 37° C. for 18 hours with agitation (150 rpm). Cells were harvested by centrifugation (10,000×g for 10 minutes at 4° C.) and subsequent operations were performed at 4° C. Cells were washed with 0.01M phosphate buffer, pH 7.2, containing 170 mM NaCl (PBS), sedimented by centrifugation, and the pellets were resuspended in the same buffer to a calculated optical density of 40 at 640 nm. Cells were broken in a French Press (1400 lb/in$^2$) (American Instrument Company, Silver Spring, Md.) and cell debris was removed by centrifugation (5000×g for five minutes). OMP were sedimented from the supernatant fluid by centrifugation at 200,000×g for 1 hour. Pellets were resuspended in 0.01M HEPES (N-2 hydroxyethyl piperazine-N'-2 ethane sulfonic acid) buffer, pH 7.4, at an approximate protein concentration of 20 mg/ml. The protein solutions were layered on a 35–55% (W/V) sucrose gradient prepared in 0.01M HEPES buffer and OMP were pelleted by centrifugation at 131,000 ×g for thirty-six hours. The OMP were resuspended in 0.01M HEPES buffer containing 1 Mm MgCl$_2$ and sedimented by centrifugation (200,000 ×g for 1 hour). Pellets were resuspended in the same buffer and stored at −20° C. Protein concentrations were measured according to the procedure described above.

Immunoblotting

OMP (50 ug) and purified VT-1 and VT-2 (3–5 ug) were separated into individual protein bands by sodium dodecyl sulfate (SDS) —polyacrylamide gel electrophoresis. The gels were run in a double slab electrophoresis cell (Protean, Bio-Rad Laboratories, Richmond, Calif.) at a constant voltage of 200 V until bromophenol dye reached 1 cm from the bottom of the gel. After electrophoresis, protein bands were transferred to a PVDF membrane (IMMOBILIM TM, Millipore, Bedford, Mass.) in a buffer containing 25 ,mM Tris, 192 mM glycine and 20% methanol (W/V) using a transblot apparatus (Bio-Red Laboratories, Richmond, Va.) at 30 V for 18 hours. The membrane was stained immunochemically as follows. Nonspecific binding sites were blocked by incubation with 5% BSA in TBS for 1 hour at 37° C. After rinsing the gel with 1% BSA in TBS, the PVDF membrane was incubated with monoclonal antibody 4E8C12 (Ascites fluid diluted 1:6000 in TBS) for i hour at 37° C. The membrane was washed 3 times with TBS plus 0.05% Tween-20 (TBS-T) and was incubated with alkaline phosphatase-labeled goat-anti-mouse (IgG diluted 1:2000 in TBS) for 30 minutes at 37° C. The membrane was washed thoroughly with TBS-T [+0.05% SDS] and treated with BCIP/NBT phosphatase substrate (Kirkegaard & Perry Laboratories, Inc., Gaithersburg, Md.) to detect protein bands. Low molecular weight standards (Electrophoresis Calibration Kit, Pharmacia, Piscataway, N.J.) were run on each gel and each was stained with 0.25% Commassie brilliant blue R-250 (Imperial Chemical, London) before and after transfer, to document the transfer of proteins.

EXAMPLE II

Determination of Sensitivity of the Monoclonal Antibody

Figure 2:
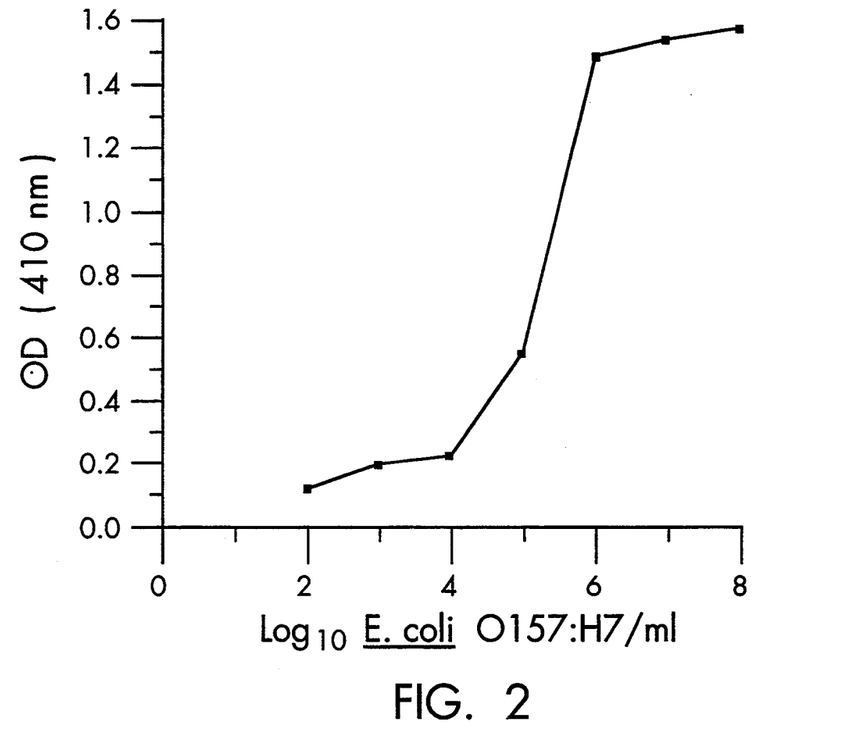
FIG. 2 is a graph illustrating the sensitivity of the monoclonal antibody 4E8C12 in a direct ELISA for detecting *E. coli* 0157:H7, strain 932, as described in Example II.

The sensitivity of the monoclonal antibody was determined using a direct ELISA with various levels of 8 different strains of *E. coli* 0157:H7. The detection limit was in the range of $10^4$ to $10^5$ cells/mi. An example is shown in FIG. 2 which illustrates the sensitivity of monoclonal antibody 4E8C12 in a direct ELISA for detecting *E. coli* 0157:H7, strain 932.

EXAMPLE III

Specificity of the Monoclonal Antibody

The specificity of the monoclonal antibody was determined by examining the cross-reactivity with different enteric bacteria. The following bacteria listed in Table 2 of Example I were tested according to the procedures of Example I. The results are presented below in Table 2.

TABLE 3

Reactivity of MAb 4E8C12 with *E. coli* 0157:H7 and Other Enteric Bacteria

| Organism | No. of Strains Tested | No. Positive[a] |
|---|---|---|
| *Escherichia coli* | | |
| 0157:H7 | 36 | 36 |
| 0157:H16 | 1 | 0 |
| 0157:H19 | 1 | 0 |
| 0157:H25 | 1 | 0 |
| 0157:H45 | 1 | 0 |
| 0157:H− | 1 | 0 |
| 02:K1:H7 | 1 | 0 |
| 026:H116 | 5 | 5 |
| 028ac | 1 | 0 |
| 0111 | 3 | 0 |
| 0113 | 1 | 0 |
| 0124 | 1 | 0 |
| 0128 | 1 | 0 |
| Additional serotypes other than 0157:H7 or 026:H11 | 23 | 0 |
| *Escherichia hermanii* | 1 | 0 |
| Proteus spp. | 3 | 0 |
| *Klebsiella pneumoniae* | 13 | 0 |
| *Klebsiella oxytoca* | 1 | 0 |
| Cytrobacter spp. | 11 | 0 |
| *Serratia marcescens* | 1 | 0 |
| *Shigella dysenteriae* | 2 | 0 |
| Salmonella spp. | 17 | 0 |
| *Campylobacter jejuni* | 5 | 0 |
| *Yersinia enterocolitica* | 12 | 0 |
| *Enterobacter cloacae* | 2 | 0 |
| *Hafnia alvei* | 1 | 0 |
| *Aeromonas hydrophila* | 4 | 0 |

[a]OD$_{410}$ value of 0.2 above background was considered positive; all positive strains had OD values > 1.0 above background.
[b]*E. coli* 026:H11 were isolated from patients with hemolytic uremic syndrome or hemorrhagic colitis.

Discussion of Results

The MAb was highly reactive with all 36 strains of *E. coli* 0157:H7 as determined by ELISA, with an O.D. of >1.0 for all strains tested. The specificity of Mab 4E8C12 was determined by ELISA using *E. coli* strains other than serotype 0157:H7 and several strains of *Y. enterocolitica*, Salmonella spp., *Enterobacter cloacae*, *C. jejuni*, *S. dysenteriae*, Proteus spp., *A. hydrophila*, *Hafnia alvei*, *K. pneumoniae*, *K. oxytoca*, *S. marcescens* and Citrobacter spp. Five strains other than serotype 0157:H7, i.e., all *E. coli* 026:H11, reacted with the Mab (Table 2). These strains were isolated from patients with hemolytic uremic syndrome or hemorrhagic colitis and produce verotoxin identical to that produced by *E. coli* 0157:H7.

From the examples disclosed, one skilled in the art will appreciate that the monoclonal antibody disclosed above may be utilized in a variety of ways with respect to the antigen for which it has been shown to be specific. Thus, it may be used to assay *E. coli* 0157:H7 and 026:H11 in other ELISAs than sandwich ELISAs of the sort disclosed. It may be used as well in other conventional methods for utilizing an antibody for assay and other purposes, whether by utilization of immunofluorescence, immunoperoxidase reactions, or other such techniques.

EXAMPLE IV

Development of a Rapid and Sensitive Method to Detect and Isolate *E. coli* 57:H7

Bacterial strains

*E. coli* 157:H7 strains 933, 505B, 932, CL-8 and 32381 were used for inoculation studies to determine the sensitivity of the enrichment-ELISA procedure. Strains 933 and 505B were isolated from beef, whereas strains 932, CL-8, and 32381 were human isolates. These plus twenty other strains of *E. coli* 157:H7, *E. coli* of serotypes 0157:H16, 0157:H19, 0157:H25, 0157:H45, and *E. coli* K-12, were used for evaluation of the ELISA procedure only.

Monoclonal antibody production

Ascitic fluid of monoclonal antibody 4E8C12 IgG2a, specific for enterohemorrhagic *E. coli* 0157:H7 and 026:H11, was obtained from BALB/c mice injected with $10^6$ hybridoma (4E8C12) cells. Ascitic fluid was stored at −20° C. until used.

Enhancement of expression by *E. coli* 0157:H7 of antigens recognized by MAb 4E8C12

*E. coli* 0157:H7 strain 932 was grown in modified Trypticase soy broth (mTSB); comprised of (per liter) Trypticase soy broth (TSB; 30 g) [BBL Microbiology Systems, Cockeysville, Md.], bile salts No. 3 (1.5 g), K2HPO4 (1.5 g) and novobiocin (20 mg) with agitation (150 rpm) at 37° C. for 16 h. Several different growth factors were added individually or in combination to mTSB to increase the sensitivity of the ELISA. The growth factors evaluated included 1% glucose, rhamnose, mannose, lactose or sucrose, iron supplements such as 0.5-5% sheep red blood cells, 5-50 mg FeCl3/L, 0.5 FeSO4/L or 50 mg Fe(NH4)2(SO4)2/L, cation chelators such as 5 g Chelex 100/L (Biorad, Richmond, Calif.) or 0.01 and 0.05% EDTA, 0.5, 2, 5, 8 and 10 mg acriflavin-HCl/L, and 0.5 and 1% casamino acids. In addition, different growth media such as TSB, mTSB and antibiotic medium no. 3 (PAB) and different growth temperatures (300° C., 37° C. and 42° C.) with or without agitation (150 rpm) were evaluated. Following growth, cells were sedimented by centrifugation (1500 ×g, 10 min) then resuspended in 50 mM carbonate buffer, pH 9.6, and adjusted to an optical density (OD) of 640 of 0.5 (ca. $10^8$ cells/ml). The cell suspension was serially (1:10) diluted in carbonate buffer to ca. $10^4$ cells/ml, and 100 μl of each serial dilution was applied in duplicate to wells of 96-well polystyrene EIA-RIA plates (GIBCO, Grand Island, N.Y.). These cell preparations were used in a direct ELISA procedure to determine the extent of expression of the *E. coli* 0157:H7 antigens reacting with MAb 4E8C12. Higher expression of the antigen resulted in a lower detection limit of the ELISA (higher sensitivity). All experiments were replicated twice.

Media preparations

The enrichment medium, mTSB without novobiocin (dmTSB) plus casamino acids (10 g/L) and acriflavin-HCl (10 mg/L) (dmTSB-CA), was prepared by first autoclaving dmTSB plus casamino acids at 121° C. for 15 min. This was allowed to cool to room temperature, then an aqueous solution of filter-sterilized acriflavin-HCl was added. For enrichment of *E. coli* 0157:H7 in dairy products, dmTSB-CA with buffer consisting of 1.35 g KH2PO4 and 12 g Na2HPO4 per L (dmTSB-CA-buf) was used instead of 1.5 g K2HPO4 per L.

MacConkey-sorbitol agar (Difco Laboratories, Detroit, Mich.) with 4-methylumbelliferone β-D-glucuronide (0.1 g/L) (MSA-MUG) was used for isolation of *E. coli* 0157:H7 from enrichment culture.

Inoculation studies

Fresh retail ground beef, raw milk, pasteurized whole and skim milk, and Cheddar, Swiss, Colby and brick cheese were inoculated with different levels of *E. coli* 0157:H7 to determine the sensitivity of the detection procedure. Aerobic plate counts were done on each product before inoculation using plate count agar and incubating plates at 30° C. for 48 h. Inocula of *E. coli* 0157:H7 were prepared by growing individually the five strains for 16 h at 37° C. in TSB. Cells were sedimented by centrifugation 1500 ×g for 10 min and resuspended in 0.01 M phosphate buffered saline, pH 7.2, (PBS) to an $OD_{640}$ of 0.5 (ca. $10^8$ css CFU/ml). Cells were diluted appropriately in PBS to obtain 5 to 22.5 *E. coli* 0157:H7 per 300 μl which was inoculated into 25 g of product. Actual inoculum levels were determined by culturing dilutions of inocula on TSA plates at 37° C. for 16 h. Each strain of *E. coli* 0157:H7 was tested individually. Uninoculated samples of each product were included in each study as a control.

Ground beef samples (25 g each) were added individually to 225 ml of dmTSB-CA broth in 1-L Erlenmeyer flasks, and dairy products (25 g each) were added to 225 ml of dmTSB-CA-buf for enrichment of *E. coli* 0157:H7. All samples were incubated at 37° C. for 16–18 h with agitation (150 rpm). After incubation, *E. coli* 0157:H7 was detected in enrichment cultures by a sandwich ELISA procedure.

The ELISA was performed in 96-well polystyrene EIA-RIA plates (GIBCO). Each well was coated with 100 μl of affinity purified goat antibody to *E. coli* 0157:H7 (10 μg/ml in 50 mM carbonate buffer, pH 9.6) [Kirkegaard and Perry Laboratories, Gaithersburg, Md.] and incubated at room temperature for 1 h or overnight. The antibody solution was removed by aspiration and the remaining binding sites were blocked with milk diluent/blocking solution [Kirkegaard and Perry Laboratories]for 15 min at room temperature. Blocking agent was removed and 300 μl of enrichment culture was added per well and incubated at 37° C. for 45 min. After washing the wells three times with 50 mM Tris, pH 7.5, containing 150 mM NaCl and 0.05% Tween-20 (TBS-T), 100 μl of MAb 4E8C12 (ascitic fluid diluted 1:6000 in TBS) was added and incubated at 37° C. for 45 min. The wells were washed three times with TBS-T followed by the addition of 100 μl of goat anti-mouse IgG conjugated to horseradish peroxidase (1:1400 in TBS) [Kirkegaard and Perry Laboratories] and incubated at 37° C. for 45 min. After washing the wells four times with TBS-T, 100 μl of 2,2'-azino-di[3-ethylbenzthiazoline sulfate]-peroxidase substrate was added per well and held at room temperature for 20 min. The reaction was stopped by adding 50 μl of 1% sodium dodecyl sulfate in TBS per well and the OD of each well was measured at 410 nm by a Dynatech MR600 microplate reader. An OD of 0.2 above background was considered as positive. In each assay, enrichment cultures of food samples without inoculated $E.$ $coli$ 0157:H7 were included as controls, and these were used to establish background readings.

Samples positive by sandwich ELISA were considered presumptive positive for $E.$ $coli$ 0157:H7. $E.$ $coli$ 0157:H7 was then isolated from enrichment cultures by a cultural method. Decimal dilutions of enrichment cultures were made to $10^{-6}$ in 0.1% peptone water. Dilutions (0.1 ml) at $10^{-5}$ and $10^{-6}$ were surface plated onto MSA-MUG and incubated at 37° C. for 16-18 h. The number of colonies which were sorbitol negative (white) and MUG-negative (no fluorescence under UV light) were recorded. Five sorbitol-negative, MUG-negative colonies were picked randomly and were confirmed as $E.$ $coli$ 0157:H7 according to biochemical properties with the API 20E miniaturized diagnostic kit (Analytab Products, Plainview, N.Y.), by serology with 0157 and H7 antisera (Difco, $E.$ $coli$ Reference Center, Pennsylvania State University, University Park Pa.), and by Vero cell cytotoxicity assay.

The sensitivity of the sandwich ELISA was determined using pure cultures of the five strains of $E.$ $coli$ 0157:H7 at levels ranging from $10^3$ to $10^8$ CFU/ml. Each strain was tested individually. Similar studies were done with enrichment cultures of ground beef and dairy products that were spiked after enrichment with different levels of each of the same five strains of $E.$ $coli$ 0157:H7. Uninoculated enrichment cultures were used as controls. Detection and isolation of $E.$ $coli$ 0157:H7 from retail ground beef and raw milk from farms. A total of $10^7$ fresh ground beef samples were obtained from several Madison, Wis.-area grocery stores during a 5-week period (December 90–January 91). Also 115 raw milk samples from bulk tanks of 69 different farms were obtained. Samples were placed in coolers with ice and were assayed for naturally occurring $E.$ $coli$ 0157:H7 by the procedure described above within 1-2 h after being brought to the laboratory. $E.$ $coli$ 0157:H7 was isolated from positive samples and isolates were confirmed as $E.$ $coli$ 0157:H7 using the methods described above. A three-tube most probable number procedure was used to quantitate the number of $E.$ $Coli$ 0157:H7 in positive ground beef samples. Ground beef samples were added (25 g, 2.5 g and 0.25 g) to 225 ml, 247.5 ml and 250 ml of dmTSB-CA, respectively, in Stomacher bags (3 per sample size), and macerated by a Stomacher for 5 min. The samples were transferred to sterile 1-L Erlenmeyer flasks and incubated at 37° C. for 18 h with agitation (150 rpm). The presence of $E.$ $coli$ 0157:H7 in positive cultures (flasks) was confirmed by streak plating a loopful of enrichment culture on MSA-MUG plates. The plates were incubated at 37° C. for 16-18 h and white (sorbitol-negative), MUG-negative colonies were selected and verified as $E.$ $coli$ 0157:H7 by the confirmatory assays described above.

Results

Figure 3:
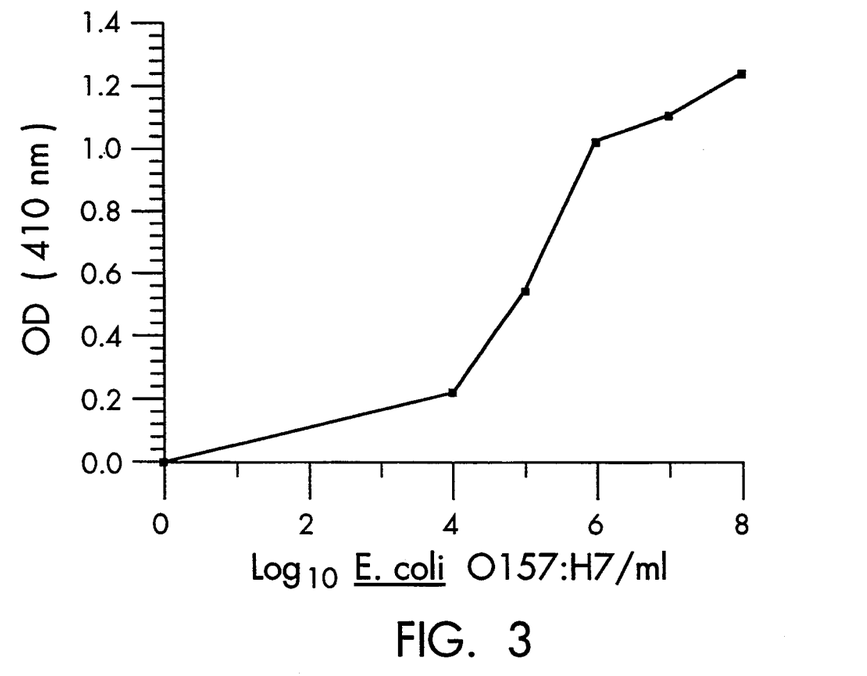
FIG. 3 is a graph illustrating the sensitivity of a sandwich ELISA to detect *E. coli* 0157:H7 strain 932 in pure culture grown in mTSB with agitation.

A sandwich ELISA was developed for detecting $E.$ $coli$ 0157:H7 in enrichment cultures of food. The specificity of the ELISA was determined using several strains of $E.$ $coli$ 0157:H7 and $E.$ $coli$ 0157:non-H7. All 25 strains of $E.$ $coli$ 0157:H7 reacted strongly in ELISA, whereas $E.$ $coli$ 0157:H16, 0157:H19, 0157:H25, and 0157:H45 were all negative. The sensitivity of the assay was determined with $E.$ $coli$ 0157:H7 (five different strains tested individually) in pure culture and in enrichment cultures of foods. The minimum number of cells detectable in pure culture was in the range of $10^4$–$10^5$ CFU/ml, as illustrated in FIG. 3, and in enrichment cultures of food spiked with different levels of $E.$ $coli$ 0157:H7 after enrichment was in the range of $10^5$–$10^6$ $E.,$ $coli$ 0157:H7/ml.

Figure 4:
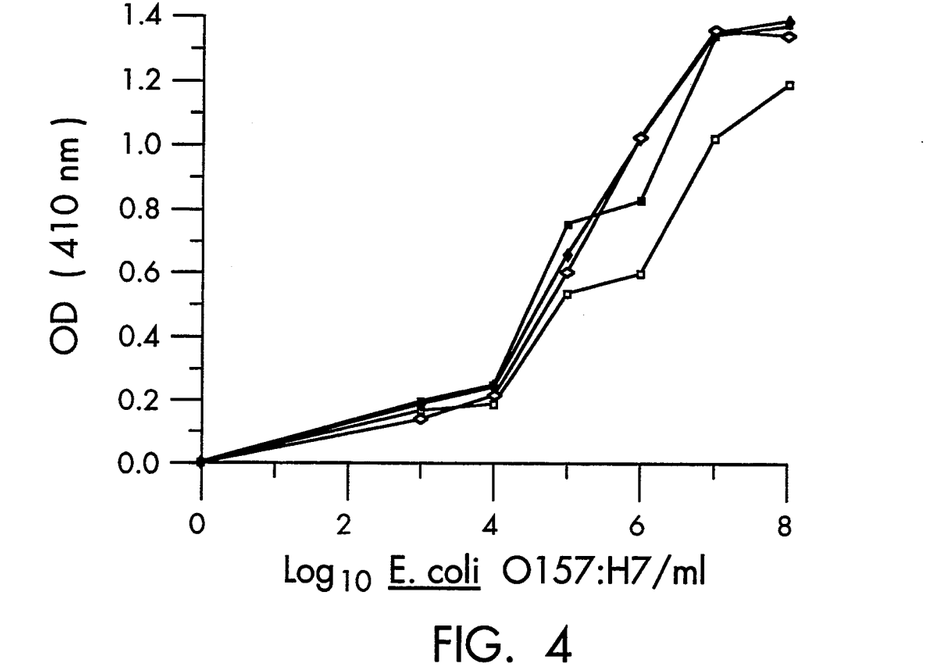
Figure 4 is a graph illustrating the effect of growth temperature on detection of *E. coli* 0157:H7 strain 932 by sandwich ELISA. The cells were grown in mTSB with or without agitation. Legend: ▲=37° C. with agitation; Δ=30° C. with agitation; ■=37° C. static; □=30° C. static.

In order to increase the sensitivity of the assay, studies were done to enhance the expression of the antigens on the bacterial surface which are recognized by the MAb. Standard enrichment conditions for isolating $E.$ $coli$ 0157:H7 from foods have been culturing in mTSB at 37° C. with agitation. Hence, results from studies with these conditions were used as the standard for comparison. The effect of two growth temperatures (30° and 37° C.) and agitation of the enrichment culture on expression of these antigens is shown in FIG. 4. These variables had no substantive effect on enhancing expression of the relevant antigens as evidenced by no major decrease in sensitivity of the ELISA when compared to the standard conditions for enrichment. Growth of $E.$ $coli$ 0157:H7 in mTSB at 42° C. was poor, hence it was not possible to obtain an adequate amount of cells for detection by ELISA.

Figure 5:
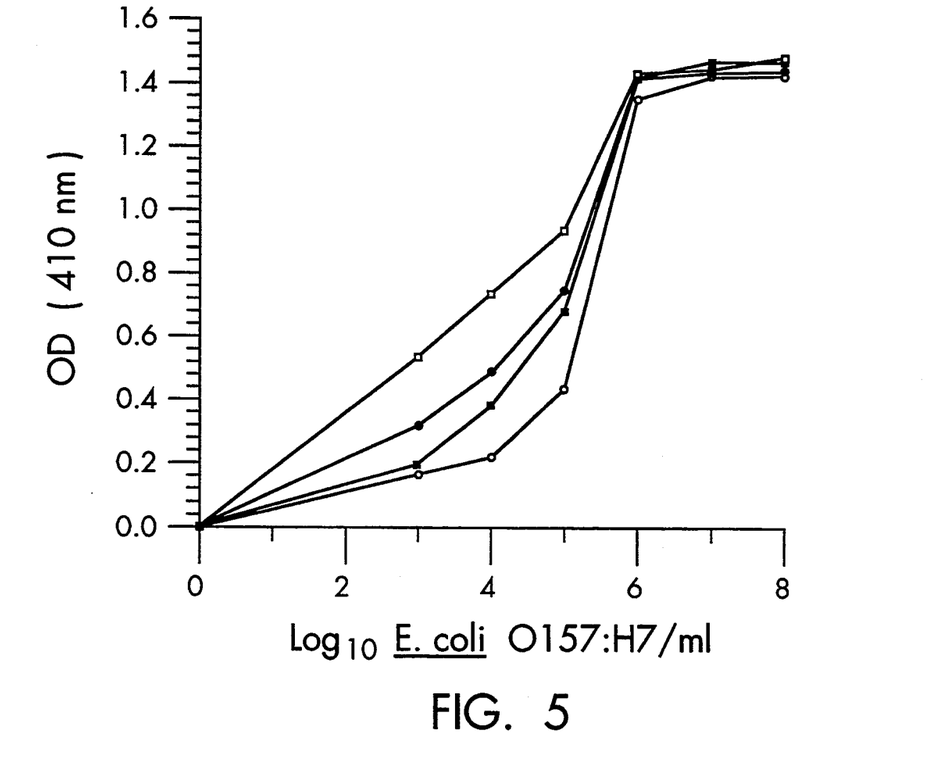
FIG. 5 is a graph illustrating the effect of acriflavin-HCl (10mg/L) and/or casamino acids (10g/L) in enrichment medium on enhancement of expression of *E. coli* 0157:H7 antigens reacting with Mab 4E8C12, as determined by ELISA. Cultures of *E. coli* 0157:H7 strain 932 were grown at 37° C. with agitation. Legend: O=mTSB; =MTSB +casamino acids; □=mTSB +acriflavin-HCl ●=mTSB+acriflavin-HCl+casamino acids.

Both acriflavin-HCl and casamino acids in mTSB had a major effect on increasing the sensitivity of the ELISA as illustrated in FIG. 5. Acriflavin-HCl at 10 mg/L decreased the detection limit from $10^4$–$10^5$ $E$ $coli$ 0157:H7/ml to $10^3$ cells/mi. Acriflavin-HCl at lower concentrations had no significant effect on decreasing the detection limit. Casamino acids at 0.5 or 1% also increased the sensitivity of the ELISA, but not as much as did the addition of acriflavin. However, the addition of casamino acids to mTSB had an extra benefit of increasing the growth rate of $E.$ $coli$ 0157:H7.

Several other substrates or growth factors also were evaluated for their effect on increasing the sensitivity of the ELISA. These included growth in TSB or antibiotic medium No. 3 (PAB) versus mTSB. mTSB was best both for growth of $E.$ $coli$ 0157:H7 and for greatest sensitivity of ELISA. The addition of 1% glucose, rhamnose, mannose, lactose or sucrose to mTSB had little effect on the sensitivity of ELISA. Similarly, the addition of iron supplements, such as sheep red blood cells (0.5–5%), $FeCl_3$ (5–50 mg/L), $FeSO_4$ (0.5 g/L), or $Fe(NH_4)_2(SO_4)_2$ (50 mg/L), had no detectable effect.

Studies to determine the efficacy of the enrichment-sandwich ELISA procedure to detect low levels of $E.$ $coli$ 0157:H7 in foods was done with five different strains of $E.$ $coli$ 0157:H7 tested individually at an inoculum of 0.2 to 0.9 cells per gram in ground beef and a variety of dairy products. The results are presented below in Tables 4 and 5.

TABLE 4

Detection of *E. coli* 0157:H7 in inculated retail ground beef by enrichment-ELISA procedure.

| Sample No. | APC[a] (CFU/g) | *E. coli* 0157:H7 counts[b] (CFU/ml) | No. of *E. coli* 0157:H7 strains detected/ No. of strains tested | Range of $OD_{410}$ of ELISA of enrichment culture[c] | Level of sensitivity of procedure (CFU/g) |
|---|---|---|---|---|---|
| 1 | $4.0 \times 10^5$ | ND[d] | 4/4 | 0.49 to 0.61 | 0.2 to 0.5 |
| 2 | $3.2 \times 10^6$ | ND | 4/4 | 0.63 to 0.89 | 0.5 to 0.6 |
| 3 | $3.8 \times 10^6$ | ND | 5/5 | 0.45 to 0.64 | 0.3 to 0.9 |
| 4 | $1.0 \times 10^9$ | ND | 1/5 | 0.36 to 0.74[e] | 0.3 to 0.9 |
| 5 | $3.0 \times 10^4$ | $3.5 \times 10^7$ | 5/5 | 0.67 to 0.98 | 0.4 to 0.6 |
| 6 | $1.7 \times 10^5$ | $3.8 \times 10^6$ | 5/5 | 0.68 to 0.92 | 0.2 to 0.4 |
| 7 | $1.6 \times 10^4$ | $4.2 \times 10^7$ | 5/5 | 0.67 to 1.09 | 0.4 to 0.6 |
| 8 | $4.8 \times 10^6$ | $8.0 \times 10^7$ | 5/5 | 0.46 to 0.95 | 0.2 to 0.6 |
| 9 | $1.1 \times 10^4$ | $2.4 \times 10^7$ | 5/5 | 0.98 to 1.12 | 0.2 to 0.6 |
| 10 | $7.8 \times 10^4$ | $1.9 \times 10^7$ | 5/5 | 0.93 to 1.05 | 0.2 to 0.6 |

[a] Aerobic plate count.
[b] No. of *E. coli* 0157:H7 in enrichment culture.
[c] Background $OD_{410}$ ranged from 0.001 to 0.181. $OD_{410}$ of 0.2 above background was considered positive.
[d] ND, not determined.
[e] Background $OD_{410}$ of this sample was 0.427; sample appeared spoiled.

TABLE 5

Detection of *E. coli* 0157:H7 in inoculated dairy products by enrichment-ELISA procedure.

| Sample | *E. coli* 0157:H7 counts[a] (CFU/ml) | No. *E. coli* 0157:H7 strains detected/No. strains tested | Range of $OD_{410}$ of ELISA of enrichment culture[b] | Level of sensitivity of procedure |
|---|---|---|---|---|
| Sharp Cheddar cheese | ND[c] | 4/5 | 0.83 to 0.93 | 0.8 to 0.9 CFU/g |
| Sharp Cheddar cheese | $3.5 \times 10^8$ | 5/5 | 0.52 to 0.99 | 0.3 to 0.6 CFU/g |
| Mild Cheddar cheese | $4.7 \times 10^7$ | 5/5 | 0.82 to 1.01 | 0.5 to 0.6 CFU/g |
| Brick Cheddar cheese | ND | 5/5 | 0.56 to 0.98 | 0.3 to 0.6 CFU/g |
| Swiss Cheese | ND | 5/5 | 0.53 to 1.09 | 0.3 to 0.6 CFU/g |
| Colby Cheese | $3.7 \times 10^8$ | 5/5 | 0.84 to 1.10 | 0.2 to 0.6 CFU/g |
| Pasteurized whole milk | $1.8 \times 10^8$ | 5/5 | 0.92 to 1.17 | 0.4 to 0.9 CFU/ml |
| Pasteurized skim milk | $3.6 \times 10^7$ | 5/5 | 0.97 to 1.15 | 0.4 to 0.9 CFU/ml |
| Raw milk | $3.8 \times 10^6$ | 5/5 | 0.55 to 0.89 | 0.5 to 0.9 CFU/ml |
| Raw milk | $4.4 \times 10^7$ | 5/5 | 0.59 to 0.92 | 0.4 to 0.8 CFU/ml |

[a] No. of *E. coli* 0157:H7 in enrichment culture.
[b] Background $OD_{410}$ ranged from 0.004 to 0.196. $OD_{410}$ of 0.2 above background was considered positive.
[c] ND, not determined.

Inoculation-recovery studies revealed that the procedure could detect between 0.2 to 0.9 *E. coli* 0157:H7 per gram of ground beef (Table 4) or dairy product (Table 5). None of the products used for these studies had naturally-occurring *E. coli* 0157:H7. Aerobic plate counts of ground beef samples before inoculation ranged from $1.1 \times 10^4$ to $1 \times 10^9$ CFU/g. All strains of *E. coli* 0157:H7 inoculated at levels of 0.2 to 0.9 CFU/g were detected in 9 of 10 ground beef enrichment samples. Only one of five inoculated strains was detected in one ground beef sample; however, this beef had an exceptionally high APC ($1 \times 10^9$ CFU/g) which is very abnormal. Ground beef with APC at this level is usually spoiled. The large number of spoilage bacteria in this sample likely suppressed the growth of *E. coli* 0157:H7 during enrichment.

*E. coli* 0157:H7 inoculated in beef or dairy products at 0.2 to 0.9 CFU/g grew in enrichment cultures to levels of $3.8 \times 10^6$ to $3.7 \times 10^8$ CFU/g. The initial pH of enrichment medium dmTSB-CA (used for ground beef) was 7.0, whereas that of dmTSB-CA-buf (used for dairy products) was 7.4. Following enrichment, the pH values were in the range of 6.5 to 6.8.

*E. coli* 0157:H7 was detected in 3 of 107 (2.8%) ground beef samples from Madison, Wis.—area grocery stores. APC of these samples before enrichment ranged from $4.0 \times 10^5$ to $7.8 \times 10^7$ CFU/g. The number of *E. coli* 0157:H7 in enrichment cultures of positive samples ranged from $2.5 \times 10^6$ to $8.6 \times 10^6$ CFU/ml, and the $OD_{410}$ of ELISA of positive enrichment cultures were 0.53 to 1.10. The organism was isolated by cultural procedures from all 3 samples that were *E. coli* 0157:H7-positive by ELISA. MPN determinations revealed *E. coli* 0157:H7 populations of 0.4 to 1.5 cells/g in the three samples.

A survey of 115 raw milk samples from 69 different farms revealed *E. coli* 0157:H7 was detected in 13 samples and was culturally confirmed in 11 samples. These 11 samples came from 7 different farms. APC of all milk samples before enrichment ranged from $2.8 \times 10^2$ to $2.6 \times 10^5$ CFU/ml. The $OD_{410}$ of ELISA of *E. coli* 0157:H7-positive enrichment cultures were 0.55 to 1.08.

It is understood that the present invention is not limited to the particular reagents, steps or methods disclosed herein. Instead it embraces all such modified forms thereof as come within the scope of the following claims:

What is claimed is:

1. A diagnostic kit for detecting the presence of *E. coli* 0157:H7, *E. coli* 026:H11, or both, comprising a monoclonal antibody which specifically binds to *E. coli* 0157:H7 and *E. coli* 026:H11 prepared from hybridoma ATCC HB 10452 in one or more container and directions for its use.

2. The diagnostic kit of claim 1, wherein the monoclonal antibody is conjugated to a label.

3. The diagnostic kit of claim 2, wherein the label is selected from the group consisting of enzymes, radioisotopes, particulate labels, chromogens, fluorescers, chemiluminescers, coenzymes, free radicals, and bacteriophages.

4. The diagnostic kit of claim 1, wherein the monoclonal antibody is bound to a support.

5. A diagnostic kit for differentiating enterohemorrhagic E. coli 0157:H7 and E. coli 026:H11 from other E. coli and enteric pathagens based upon an outer membrane protein unique to enterohemorrhagic E. coli 0157:H7 and E. coli 026:H11 comprising a monoclonal antibody which specifically binds to the same epitope bound by monoclonal antibody 4E8C12 and directions for its use.

6. The diagnostic kit of claim 5, wherein the monoclonal antibody is produced by hybridoma ATCC HB 10452.

7. An immunoassay method for the detection of E. coli 0157:H7 or E. coli 026:H11, which comprises
    (a) contacting a sample suspected of containing E. coli 0157:H7 or E. coli 026:H11 with a monoclonal antibody which specifically binds to the same epitope bound by monoclonal antibody 4E8C12 in order to form an immune complex, and
    (b) determining the presence of the complex in order to detect E. coli 0157:H7 or E. coli 026:H11 in the sample.

8. The method of claim 7, wherein the monoclonal antibody is prepared from the hybridoma ATCC HB 10452.

9. The method of claim 7, wherein the monoclonal antibody is conjugated to a label.

10. A bioreagent for antibody assays comprising a substantially pure protein found in the outer membrane of E. coli 0157:H7 or E. coli 026:H11 having a molecular weight between about 5000 and 6,000 daltons, said protein being specifically bound by a monoclonal antibody which specifically binds to the same epitope specifically bound by monoclonal antibody 4E8C2.

11. A substantially pure outer membrane protein harvestable from E. coli 0157:H7 or E. coli 026:H11, the outer membrane protein having a molecular weight between about 5,000 and 6,000 daltons, and which specifically binds to monoclonal antibodies secreted by hybridoma ATCC HB 10452.

12. A method for detecting the presence of an antigen wherein the antigen is an outer membrane protein of E. coli 0157:H7 on a sample comprising
    (a) culturing the sample in a selective enrichment medium containing acriflavin to form an enriched culture, and
    (b) detecting the E. coli 0157:H7 outer membrane antigen in the enriched culture.

13. The method of claim 12 wherein the sample is a food product.

14. The method of claim 12 wherein the assay is an ELISA assay.

15. The method of claim 14 wherein the assay is a sandwich ELISA assay.

16. The method of claim 12 wherein the enrichment medium is a modified trypticase soy broth, containing Trypticase soy broth, bile salts, $K_2HPO_4$ novobiocin.

17. The method of claim 16 wherein the enrichment medium contains quantity of acriflavin-HCl and casamino acids to enhance antigen expression by E. coli 0157:H7.

18. The method of claim 12 wherein the sample is enriched in the selective enrichment medium for approximately 16–18 hours at a temperature between approximately 30°–37° C. with agitation.

19. The method of claim 12 wherein the selective enrichment medium further includes the following components in quantities sufficient to form an enriched culture of E. coli 0157:H7: Trypticase soy broth, bile salts, $K_2HPO_4$, casamino acids and novobiocin.

20. The method of claim 19 wherein the selective enrichment medium comprises the following components in approximate quantities per liter volume: 30 g Trypticase soy broth, 1.5 g bile salt No. 3, 1.5 g $H_2HPO_4$, 10 mg acriflavin and 20 mg novobiocin.

* * * * *